(12) United States Patent
Pelegrine et al.

(10) Patent No.: US 12,721,702 B2
(45) Date of Patent: Sep. 1, 2026

(54) DEVICE FOR RETRACTING SOFT TISSUE FOR APPOSITIONAL BONE RECONSTRUCTION

(71) Applicants: André Antonio Pelegrine, Campinas (BR); Luis Guilherme Scavone De Macedo, Pindamonhangaba (BR); Geoffrey Que-Juin Moy, Hawthorne, CA (US)

(72) Inventors: André Antonio Pelegrine, Campinas (BR); Luis Guilherme Scavone De Macedo, Pindamonhangaba (BR)

(73) Assignees: André Antonio Pelegrine, Campinas (BR); Luis Guilherme Scavone de Macedo, Pindamonhangaba (BR); Geoffrey Que-Juin Moy, Hawthorne, CA (US)

( * ) Notice: Subject to any disclaimer, the term of this patent is extended or adjusted under 35 U.S.C. 154(b) by 457 days.

(21) Appl. No.: 17/927,988

(22) PCT Filed: Jul. 1, 2020

(86) PCT No.: PCT/BR2020/050241
§ 371 (c)(1),
(2) Date: Nov. 28, 2022

(87) PCT Pub. No.: WO2021/237320
PCT Pub. Date: Dec. 2, 2021

(65) Prior Publication Data

US 2023/0210640 A1 Jul. 6, 2023

(30) Foreign Application Priority Data

May 29, 2020 (BR) .......................... 1020200109650

(51) Int. Cl.
*A61C 8/02* (2006.01)
*A61C 8/00* (2006.01)
*A61F 2/28* (2006.01)

(52) U.S. Cl.
CPC ............ *A61C 8/0089* (2013.01); *A61C 8/001* (2013.01); *A61F 2/28* (2013.01); *A61C 8/0016* (2013.01); *A61F 2002/2835* (2013.01)

(58) Field of Classification Search
CPC ....... A61C 8/006; A61C 8/0092; A61C 8/003; A61C 8/0031; A61C 8/0089; A61C 8/001;

(Continued)

(56) References Cited

U.S. PATENT DOCUMENTS 2,489,870 A * 11/1949 Dzus .................... A61B 17/683 411/548
2,511,051 A * 6/1950 Dzus .................... F16B 37/145 411/338

(Continued)

*Primary Examiner* — Jessica Weiss
(74) *Attorney, Agent, or Firm* — Maier & Maier, PLLC

(57) ABSTRACT

A titanium screw that permits the adaptation of PEEK (polyether ether ketone) capsules at both ends, enabling vertical and horizontal, uni or bidirectional appositional bone reconstructions. The screw has a length selected between 6, 8 and 10 mm; whereas the PEEK capsules have a diameter of 4.5 mm and a height of 1.5 mm. Accordingly, it is possible to retract the soft tissue and maintain the space necessary for bone reconstruction. By minimizing compression to the bone graft, this device optimizes tissue reconstruction, oftentimes crucial for the placement of implants.

8 Claims, 21 Drawing Sheets

(58) Field of Classification Search
CPC ... A61C 8/0016; A61F 2002/2835; A61F 2/28
USPC .................... 606/300–321, 70–71, 280–299
See application file for complete search history.

(56) References Cited

U.S. PATENT DOCUMENTS

| | | | | | |
|---|---|---|---|---|---|
| 3,529,508 | A * | 9/1970 | Cooksey | F16B 23/0038 | 411/397 |
| 4,253,509 | A * | 3/1981 | Collet | F16B 41/005 | 411/397 |
| 4,480,513 | A * | 11/1984 | McCauley | F16L 23/003 | 81/436 |
| 5,122,133 | A * | 6/1992 | Evans | A61B 17/742 | 606/301 |
| 5,647,710 | A * | 7/1997 | Cushman | F16B 35/00 | 411/397 |
| 5,769,637 | A * | 6/1998 | Morgan | A61F 2/2846 | 433/176 |
| 6,319,254 | B1 * | 11/2001 | Giet | A61B 17/8875 | 606/104 |
| 8,070,785 | B2 * | 12/2011 | Biscup | A61B 17/686 | 606/305 |
| 8,357,186 | B2 * | 1/2013 | Hadi | A61B 17/683 | 606/306 |
| 8,684,734 | B1 * | 4/2014 | Lyren | A61C 8/0024 | 433/173 |
| 9,788,862 | B2 * | 10/2017 | Mootien | A61B 17/7091 | |
| 11,617,642 | B2 * | 4/2023 | Dacosta | A61B 17/864 | 606/232 |
| 2003/0118968 | A1 * | 6/2003 | Massoud | A61C 8/0006 | 433/173 |
| 2005/0136380 | A1 * | 6/2005 | Niznick | A61C 8/0018 | 433/173 |
| 2007/0270855 | A1 * | 11/2007 | Partin | A61B 17/863 | 606/279 |
| 2008/0147127 | A1 * | 6/2008 | Tipirneni | A61B 17/746 | 606/301 |
| 2010/0023064 | A1 * | 1/2010 | Brunger | A61B 17/8605 | 606/301 |
| 2010/0042167 | A1 * | 2/2010 | Nebosky | A61M 37/00 | 606/301 |
| 2010/0145393 | A1 * | 6/2010 | Fallin | A61C 8/0016 | 606/301 |
| 2011/0071576 | A1 * | 3/2011 | Hadi | A61B 17/683 | 606/301 |
| 2011/0137356 | A1 * | 6/2011 | Kollmer | A61B 17/683 | 606/324 |
| 2011/0166572 | A1 * | 7/2011 | Ihde | A61C 8/0018 | 606/70 |
| 2011/0257689 | A1 * | 10/2011 | Fiechter | A61B 17/866 | 606/301 |
| 2013/0269165 | A1 * | 10/2013 | Marotta | A61C 8/0096 | 29/428 |
| 2014/0222087 | A1 * | 8/2014 | Greenberg | A61B 17/86 | 606/301 |
| 2015/0018890 | A1 * | 1/2015 | Ihde | A61C 8/0018 | 606/306 |
| 2015/0150653 | A1 * | 6/2015 | Vladila | A61C 8/0022 | 433/29 |
| 2016/0135861 | A1 * | 5/2016 | Kollmer | A61B 50/20 | 606/324 |

* cited by examiner

DEVICE FOR RETRACTING SOFT TISSUE FOR APPOSITIONAL BONE RECONSTRUCTION

FIELD OF THE APPLICATION

The present application for patent of invention refers to a device for retracting soft tissue for appositional bone reconstruction (called Barbell Technique), devised to enable the retraction of the soft tissue and, accordingly, enable the maintenance of the space necessary for bone reconstruction. By minimizing compression on the bone graft, this device optimizes tissue reconstruction, oftentimes crucial for the placement of dental implants.

BRIEF INTRODUCTION

It refers to a titanium screw that permits the adaptation of PEEK (polyether ether ketone) capsules at both ends, enabling horizontal, uni or bidirectional, and vertical appositional bone reconstructions.

STATE OF THE ART

The enshrined technique of guided tissue regeneration advocates the mechanical insulation and the maintenance of space to be reconstructed, by means of a membrane or physical barrier that prevents interference of cells originating from tissue adjacent to the site/tissue where reconstruction is desirable. This technique has been used for decades (Nyman et al., 1986; Buser et al., 1990), especially by periodontology (designed for regenerating periodontal tissues) and by the implant dentistry (designed for regenerating bone tissue to enable the installation of implants).

For the technique to be successful, it is crucial to secure mechanical insulation of the site as well as immobilization of the bone graft, which commonly appears in particulate form for optimization of revascularization and incorporation (Draenert et al., 2014). However, particulate bone grafts, not being structured, may move when used in appositional bone reconstruction, requiring the use of a membrane/structured barrier (i.e., reinforced with titanium).

Nevertheless, membranes and barriers with this type of reinforcement are non-resorbable and hydrophobic, which triggers the need for a second extensive surgical stage for the removal thereof and also entails greater chances of post-operatory complications when compared to hydrophilic resorbable membranes, such as, for example, collagens (Deeb et al., 2017). Moreover, the use of resorbable membranes, despite generating lower levels of complications, does not prevent compression of the adjacent soft tissue since they are not structured. This aspect favors displacement of the grafting material and, consequently, limitation of maintenance of the space necessary for effective bone reconstruction.

In this backdrop, the tent pole technique was developed that makes use of a titanium screw having the function of acting as a pillar, preventing a non-rigid resorbable membrane ends up collapsing into the bone defect (Le et al., 2010). This technique ("tent pole") enables the use of a non-rigid hydrophilic membrane for appositional bone augmentations, even when using non-structured bone grafts (i.e., particulate grafts).

Accordingly, it is possible to use a graft with greater remodeling potential and also a membrane with a lower tendency to exposure/contamination. Due to these factors, today the tent pole has been considered the technique most recommended for appositional bone reconstructions (Deeb et al., 2017).

Document US2011257689—publication date: Oct. 20, 2011—the invention relates to a bone screw having a stem comprising a tip and a longitudinal axis of the screw, and which can be anchored in a bone or part of a bone. A screw head is attached to the screw shaft. The screw shaft is substantially made of a plastic that is transparent to X-rays. A portion of the screw shaft is made of a material different from that of a core that substantially forms the screw shaft, and at least one load-bearing area is preferably made of metal or plastic, such as PEEK.

The document is about a screw with interchangeable ends, by fitting connections in its head and threaded at the tip of the screw, being applied in bone restoration mainly in the spine, unlike the proposed patent application which is for bone removal and restoration in dentistry, which comprises at the ends of the screw (1), hexagonal structure (3) that these are introduced into the inner fitting (4) of the PEEK capsule (2), that is, capable of being fitted into both ends of said screw (1).

PROBLEMS RELATING TO THE STATE OF THE ART

Although the enshrined tent pole technique is routinely used, it makes use of titanium screws which, in theory, were not developed for this specific purpose but rather to fasten bone blocks. Therefore, the specialty of implant dentistry has been using an adapted device to assure the feasibility of their main technique in appositional grafting today. The head of these screws was designed to compress a structured graft (i.e., bone block) against the bed receptor and not to prevent compression of the soft tissue adjacent to a region grafted with particulate matter. Added to this problem is the fact that these conventional screws can be applied only by buccal, and a non-negligible bone loss also occurs by the palatal/lingual side (Pelegrine et al., 2010). In this scope, developing a device that could maximize the tissue decompression in appositional reconstructions (both in the vertical and horizontal direction) and also enable bidirectional horizontal bone augmentation (i.e., by buccal and lingual/palatal) would be an important help in the field of implant dentistry. This versatility will enable this device to become a useful tool for various situations, with a high level of clinical usage.

Additionally, besides the conventional titanium screws currently used in the tent pole technique not having a head specially designed to prevent tissue compression, with the presence of encasements for installing drivers which may injure the soft tissue, titanium is not considered the best material for contact with soft tissue. It is scientific knowledge that PEEK (polyether ether ketone) proves superior to titanium in terms of adhesion, proliferation and viability of the gum fibroblasts (da Cruz et al., 2019).

OBJECTIVES AND ADVANTAGES OF THE INVENTION

The objective of the invention is to improve the tent pole technique, by developing a device that permits the use of a structure more suited to tissue decompression, as well as the reconstruction of horizontal bone defects in a bidirectional manner.

The present invention overcomes the shortcomings of the tent pole technique by making use of titanium screws (enshrined material for contact with bone tissue) that can be adapted to the remaining bone and, in sequence, be adapted PEEK capsules rounded and especially designed to enable contact with the soft tissue and to prevent tissue compression.

The PEEK is a synthetic polymer material having a color similar to the dental elements, which has been used in medical orthopedics for years and in odontology for manufacturing prosthetic components to be used in implants. It is a biocompatible material, of low molecular weight, with physical properties similar to bone tissue and has better cellular adhesion results than titanium (Cruz et al., 2019).

Moreover, in cases of bidirectional horizontal bone defects, the invention that is the object of this application enables effective reconstruction by both sides (i.e., buccal and lingual/palatal), as the screws can be transfastened to the remaining bone from buccal to palatal/lingual and PEEK capsules would subsequently be adapted on both sides. Bidirectional horizontal bone defects have traditionally been just by buccal due to a technical limitation, since in most cases it is practically impossible to adapt a screw from the inner side (i.e., lingual/palatal) and not because there is no need for this type of lingual/palatal reconstruction, as suggested in scientific literature (Pelegrine et al., 2010).

Accordingly, the device presented in this proposal will enable more effective bone reconstruction and, consequently, the installation of implants in more suitable positions, since bone reconstructions performed just by the buccal side normally culminate in implants installed in a more buccalized position.

Therefore, by enabling the installation of implants more suitably positioned, the invention now proposed will favor better aesthetic, functional and biological results in implant-supported restorations.

SPECIFICATION OF THE INVENTION

The present invention refers to the development of a single use device, for application in appositional bone reconstruction surgeries in implant dentistry. The device comprises a screw with variable length (6 mm, 8 mm or 10 mm) and PEEK capsules with 4.5 mm in diameter and 1.5 mm in height, capable of being incased at both ends of the screw(s). To enable the installation of the screws and capsules, there is a need to use a surgical Kit. This Kit contains drills for preparing the bed which will receive the screws, drivers to install the screws as well as an instrument to apply the PEEK capsules. The capsules can be positioned both beneath and outside the resorbable membrane.

The usage of device of the invention and its respective installment Kit makes it possible to perform surgeries for horizontal uni or bidirectional, and vertical appositional bone augmentation in a safe and predictable manner. The device structure prevents excessive compression of the overlying soft tissue and permits the maintenance of the particulate bone grafts in position and suitable stability during the entire healing process. In April of 2020 this novel technique was published in the periodical of the American Academy of Implant Dentistry, which is indexed to the PubMed, offered by the National Library of Medicine of the USA (Pelegrine et al., 2020).

This publication clearly showed the possibility of achieving bidirectional horizontal bone augmentation predictably by means of the technique proposed (with the use of the device described in this document). In this publication, the components of the installment Kit of the device were also shown.

DESCRIPTION OF THE DRAWINGS

The invention will now be described in its preferred embodiment, and for improved understanding, references will be made to the accompanying drawings, in which the following are represented.

DETAILED DESCRIPTION OF THE INVENTION

The device for retracting soft tissue for appositional bone reconstruction, object of this patent application, refers to a single device designed for application in appositional bone reconstruction surgeries in implant dentistry; the device comprises a titanium screw (1) with variable length and PEEK capsules (2) capable of being incased at both ends of the aforementioned screw (1).

Technically, for the installation of the screws (1) and PEEK capsules (2) there is a need to use a surgical Kit, which contains drills for preparing the bed that will receive the screws (1), drivers for installing the aforementioned screws (1), as well as an applied instrument of PEEK capsules (2), which can be positioned beneath or outside the resorbable membrane (M).

The device that is the object of the present invention and its respective installment Kit makes it possible to perform surgeries for horizontal uni or bidirectional, and vertical appositional bone augmentation in a safe and predictable manner. The device structure prevents excessive compression of the overlying soft tissue and permits the maintenance of the particulate bone grafts in position and suitable stability during the entire healing process.

Figure 1:
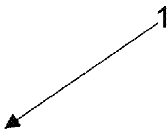
FIG. 1 shows a perspective design of the titanium screw that is the object of the device of the invention.
Figure 1:
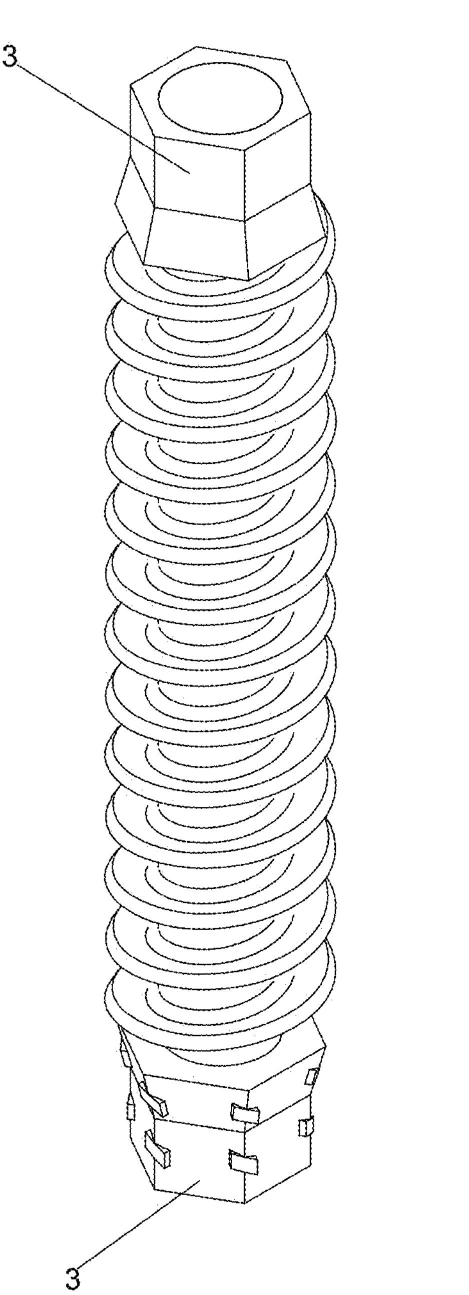
Figure 1A:
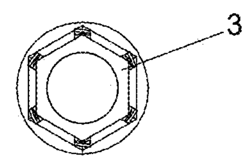
FIG. 1*a* shows the titanium screw that is the object of the device of the invention in a side view, with top and bottom views.
Figure 1A:
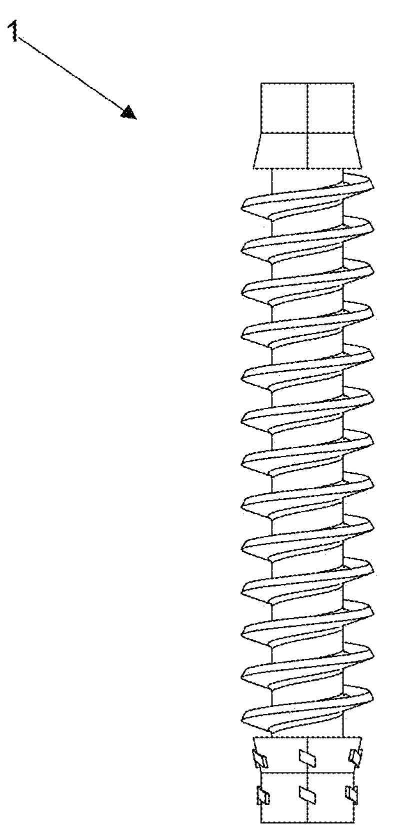
Figure 1A:
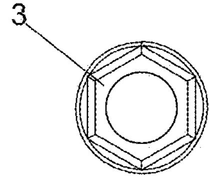
Figure 2:
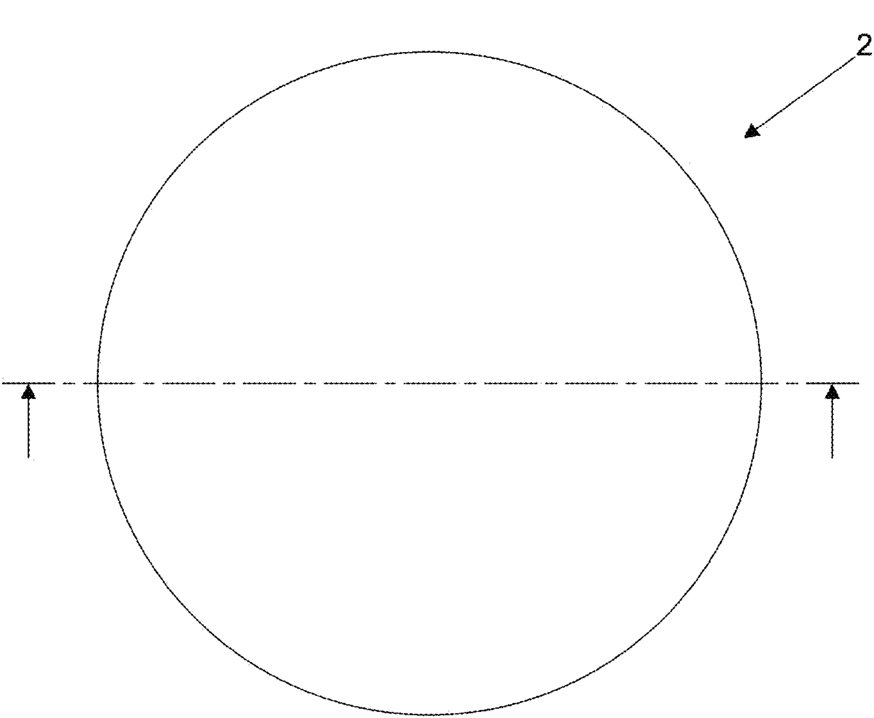
FIG. 2 shows a PEEK capsule in top view.
Figure 2A:
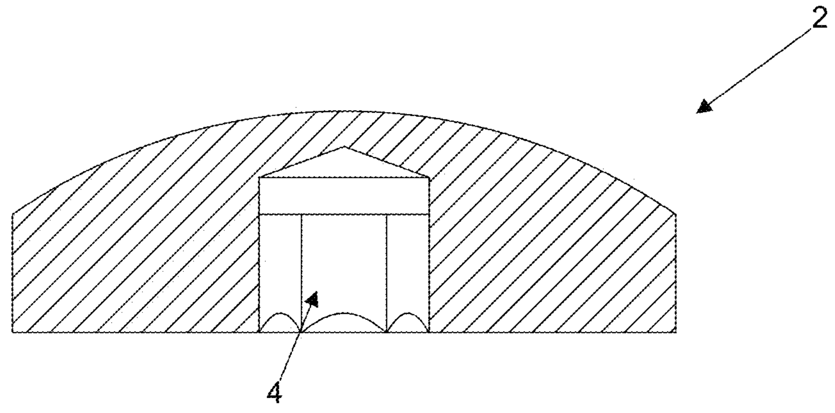
FIG. 2*a* shows a PEEK capsule according to the A-A cut indicated in the preceding figure.

FIGS. 1 to 2*a* show specific details of the screw (1) and of the PEEK capsule (2) that form the device of the invention, and the screw (1) has a length selected between 6, 8 and 10 mm; whereas the PEEK capsules (2) have a diameter of 4.5 mm and 1.5 mm in height.

Figure 1B:
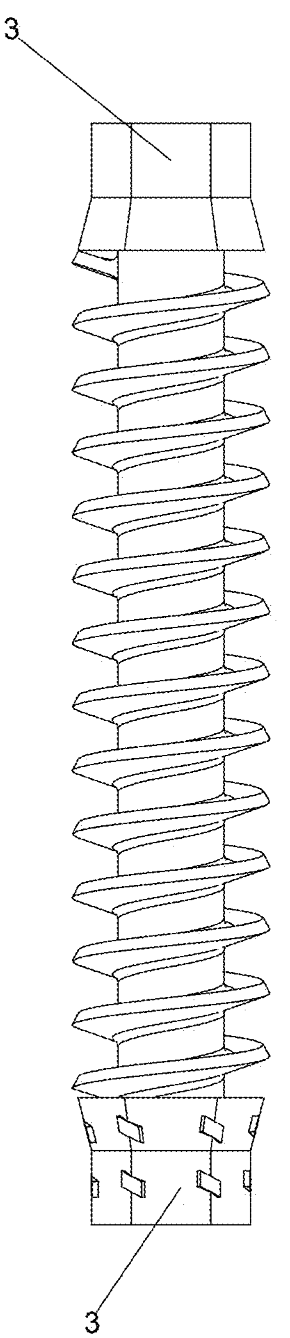
FIG. 1*b* shows the titanium screw that is the object of the device of the invention in a side view, at a rotated angle relative to the preceding figure.
Figure 1B:
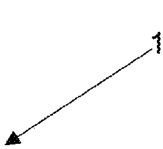

Further according to FIGS. 1 to 1*b*, the screw (1) will have the length of the threadable area varying between 8 mm, 6 mm or 4 mm; while the ends of the screw (1) present a hexagonal structure (3) measuring 1.2 mm.

FIGS. 2 and 2*a* refer to the PEEK capsule (2), which, as stated, has a capsule diameter of 4.5 mm and height of 1.5 mm, being endowed with an internal encasement (4) that permits adaptation to the hexagonal structure (3) featured at the end of the screw (1).

Figure 12:
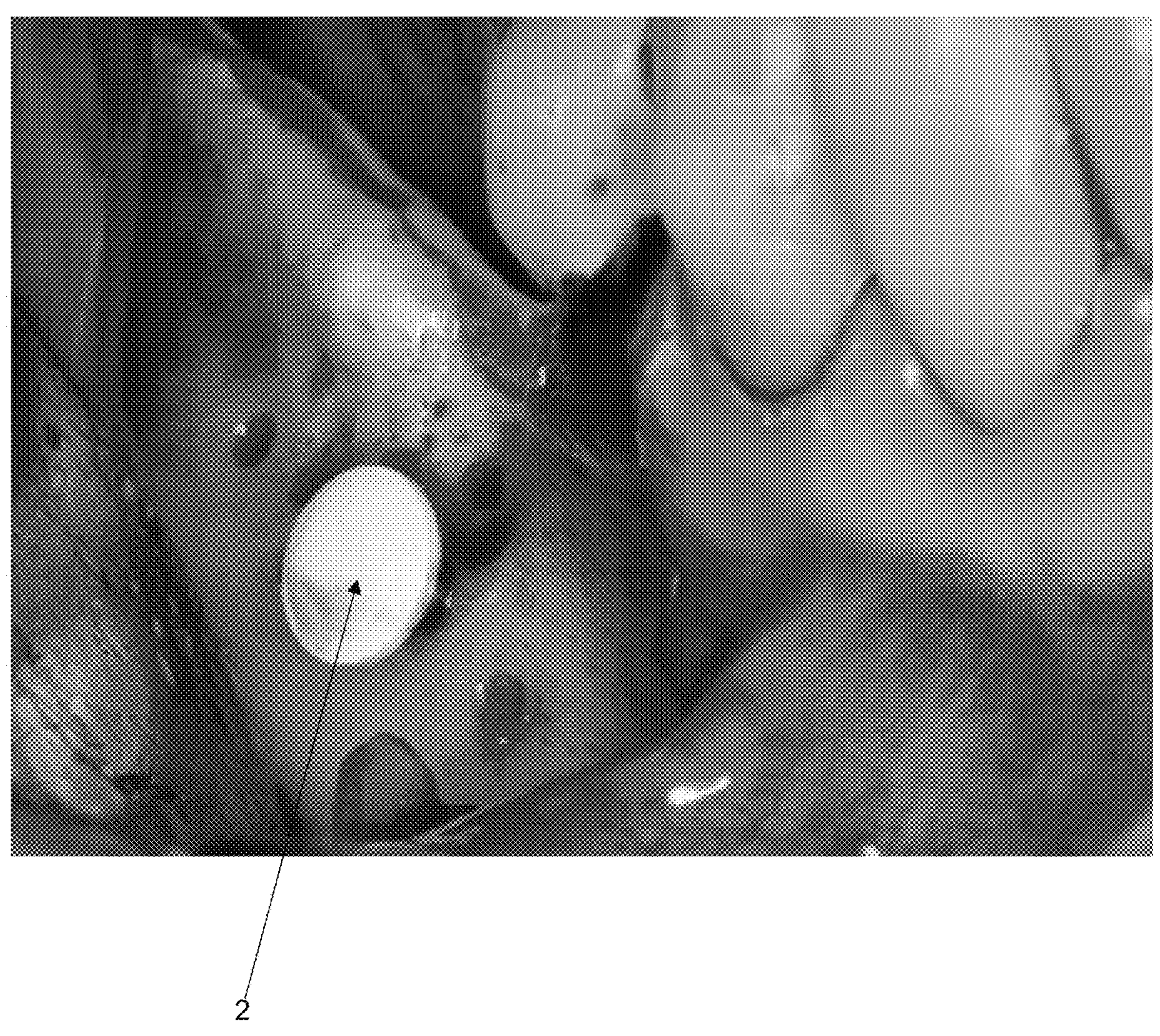
FIG. 12 shows a second clinical case in which a trans-operatory clinical image, with significant unidirectional horizontal bone loss (just by buccal) and need for tissue reconstruction prior to installing the implants; in this figure the device of the invention has already been installed, through the use of a screw 6 mm in length, since the need is solely the reconstruction of one side (buccal)
Figure 13:
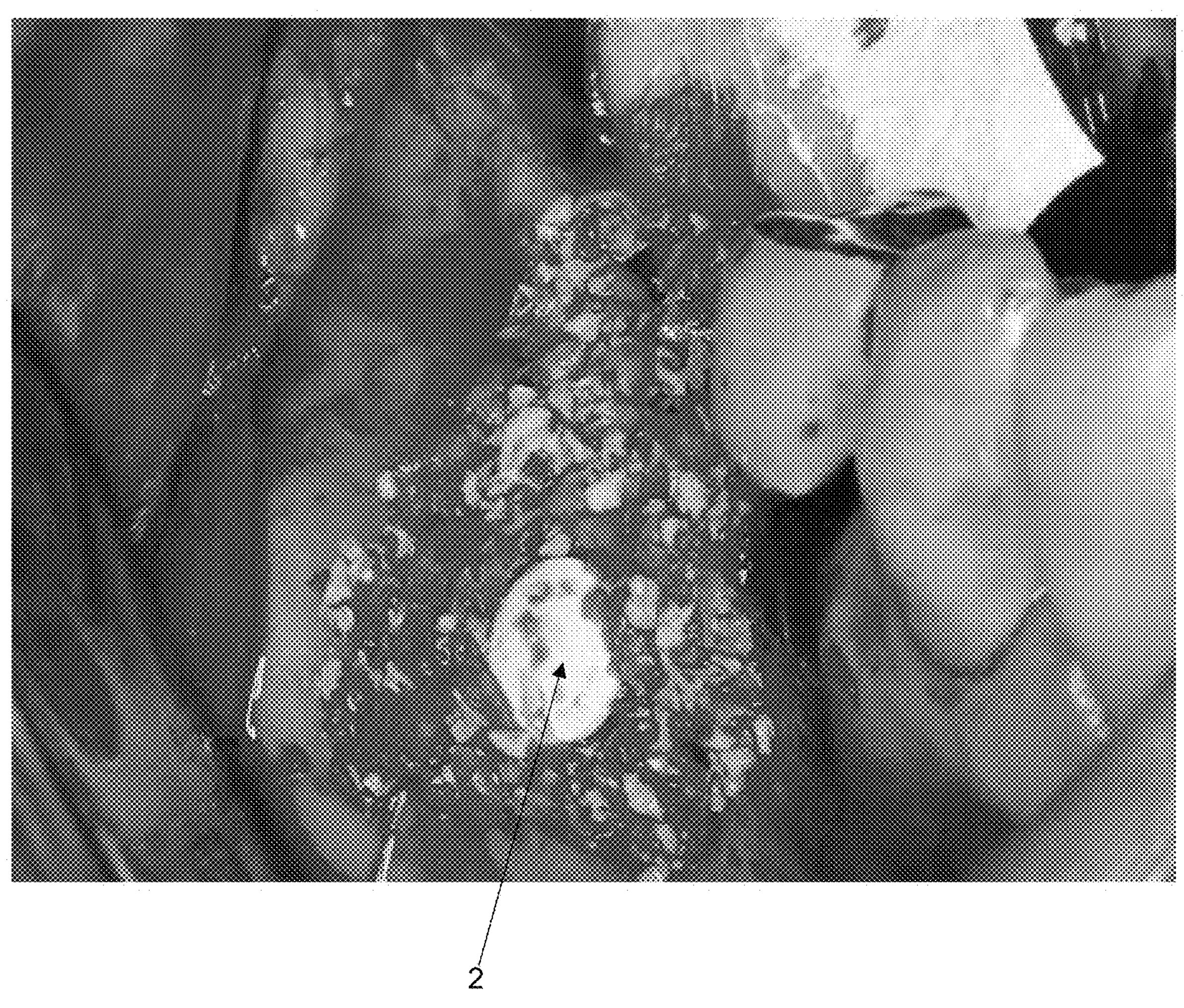
FIG. 13 shows, in the second clinical case, the adaptation of the particulate bone graft.
Figure 14:
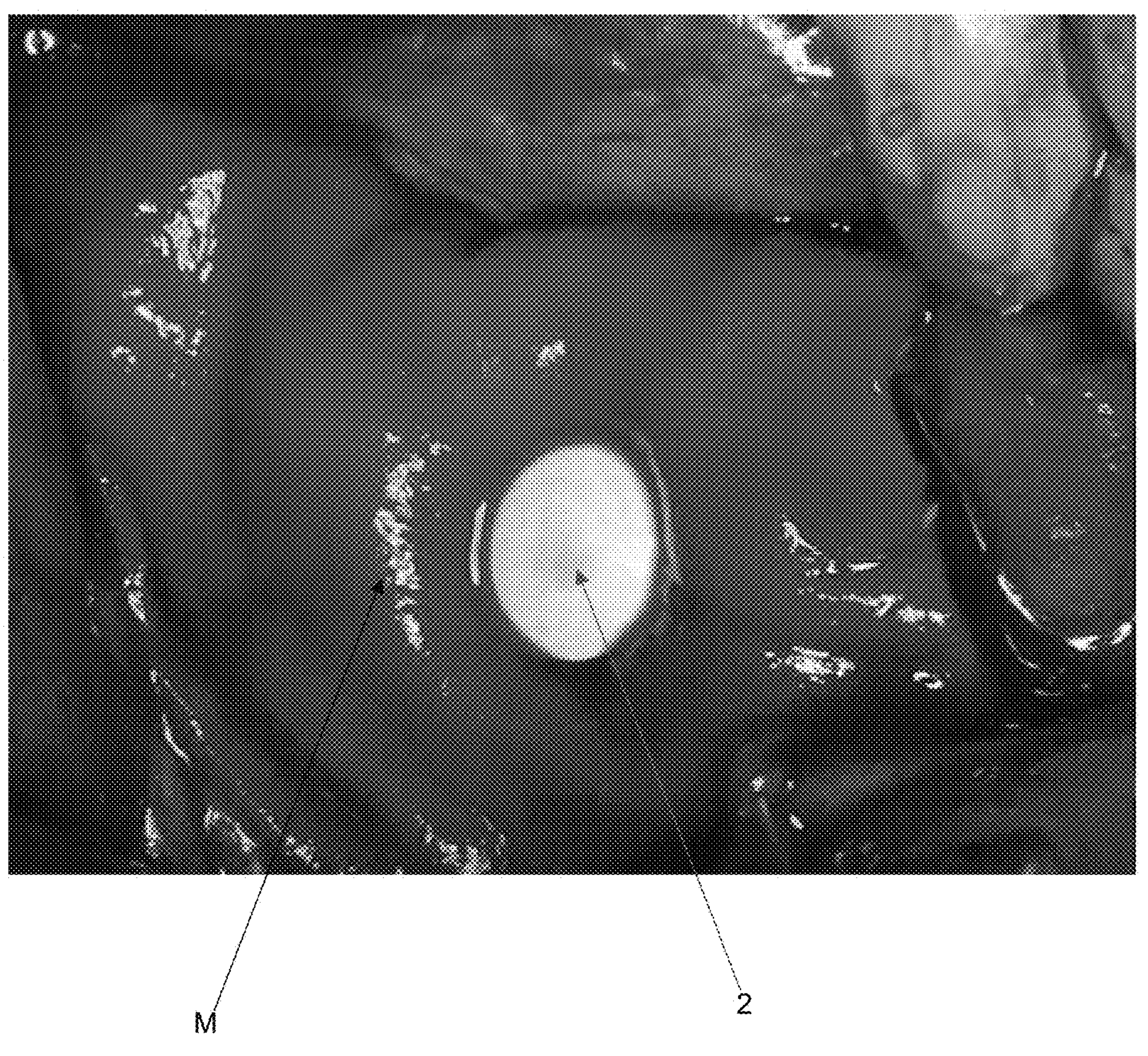
FIG. 14 shows, in the second clinical case, the coating with resorbable hydrophilic membrane; in this case, a PEEK capsule was optionally adapted on the outside of the membrane, helping to immobilize it.

It is important to emphasize that prototypes of the device for retracting soft tissue for appositional bone reconstruction (Barbell Technique) were produced and used in certain surgical procedures, which enabled the publication of the scientific article entitled "Barbell Technique™: a novel approach for bidirectional bone augmentation. Technical Note.", as previously cited in the specification of the invention. In sequence, we make use of images of the step-by-step surgery to illustrate how the device is utilized. FIGS. 3 to 11 illustrate a clinical case of bidirectional horizontal bone augmentation; FIGS. 12 to 14 demonstrate a case of unidirectional horizontal bone augmentation and FIGS. 15 to 19 a case of vertical bone augmentation, whereby illustrating the technical versatility of the device.

Figure 3:
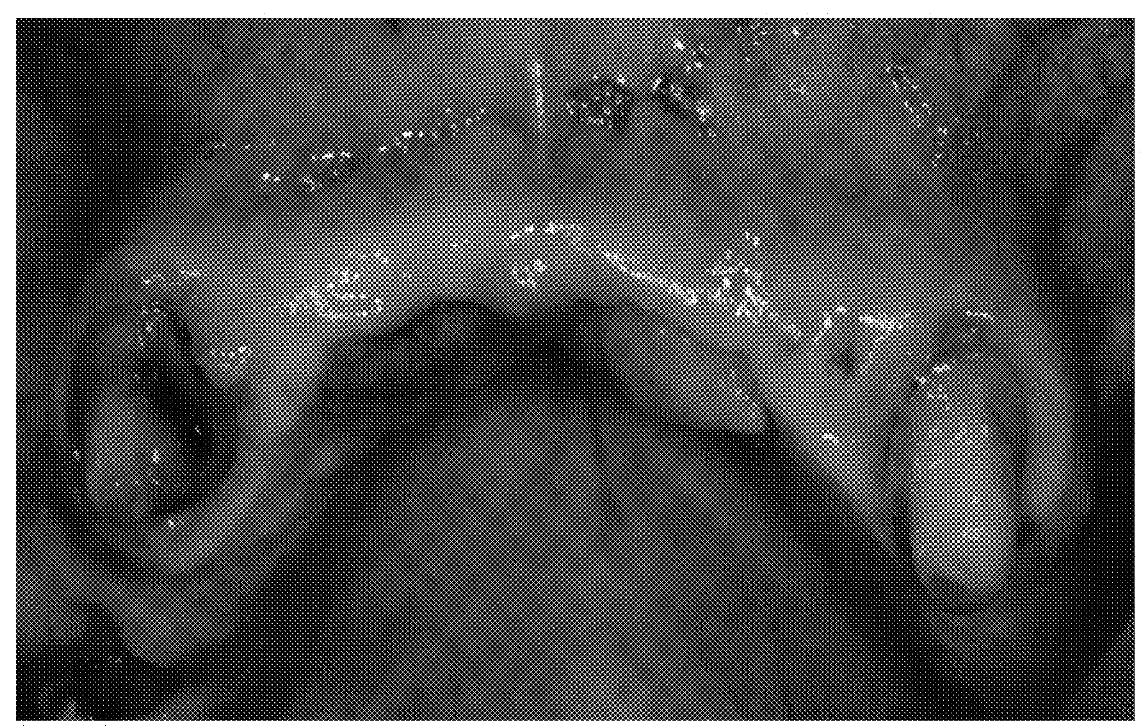
FIG. 3 shows a pre-operatory clinical situation of the first clinical case, with significant bidirectional horizontal bone loss (buccal and palatal) and the need for tissue reconstruction prior to installing the implants.
Figure 4:
FIG. 4 shows after surgical access to the bone defect, the clear need for bone reconstruction both from a buccal as well as a palatal aspect.

In more detailed fashion, FIG. 3 illustrates a pre-operatory clinical situation of the first clinical case, with significant bidirectional horizontal bone loss (buccal and palatal) and need for tissue reconstruction prior to installing the implants. After surgical access to the bone defect, there is a clear need for bone reconstruction both from a buccal as well as a palatal aspect, in accordance with FIG. 4.

Figure 5:
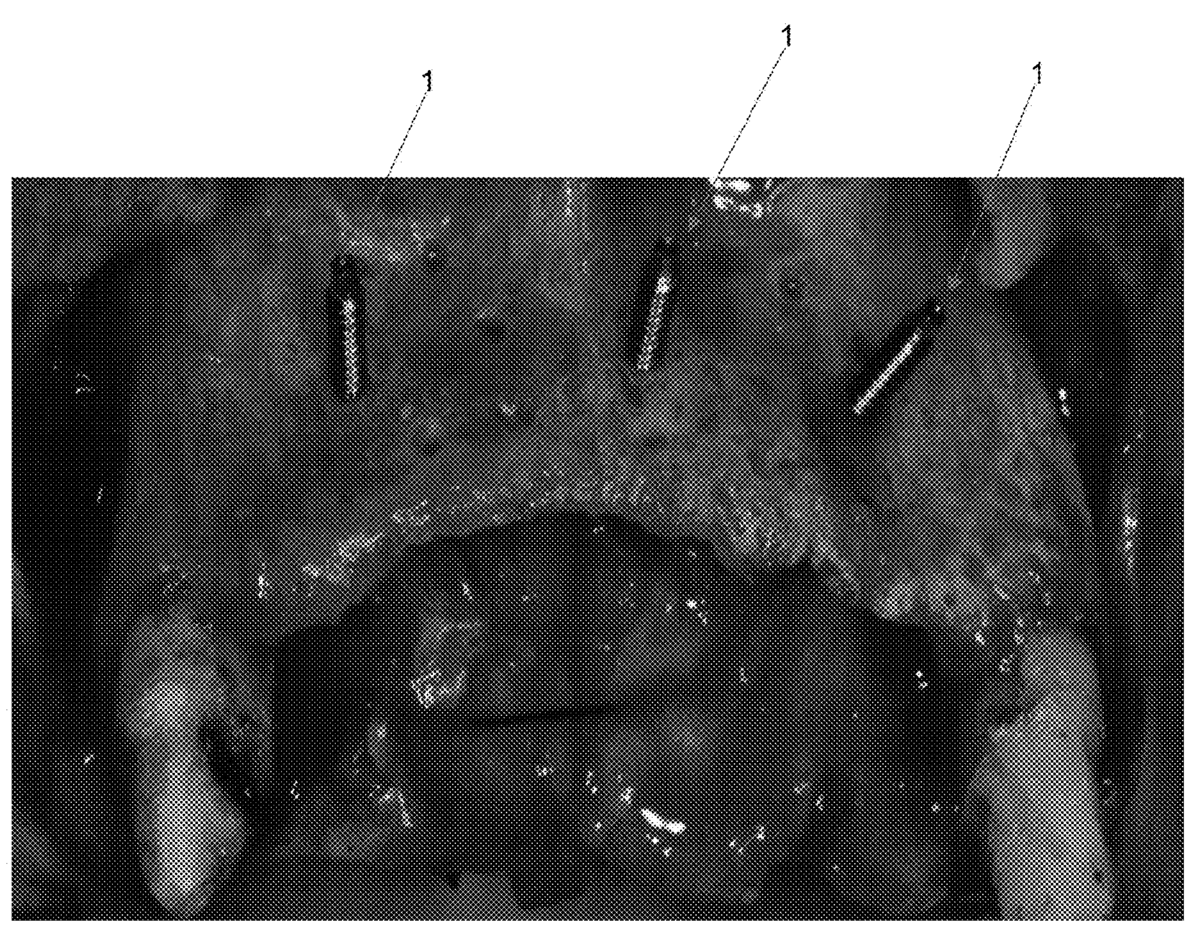
FIG. 5 shows, subsequently to creating minor perforations in the receiver bone to stimulate bleeding, making three perforations with drills measuring 1.1 mm in diameter, for the insertion of three titanium screws, illustrated therein.
Figure 6:
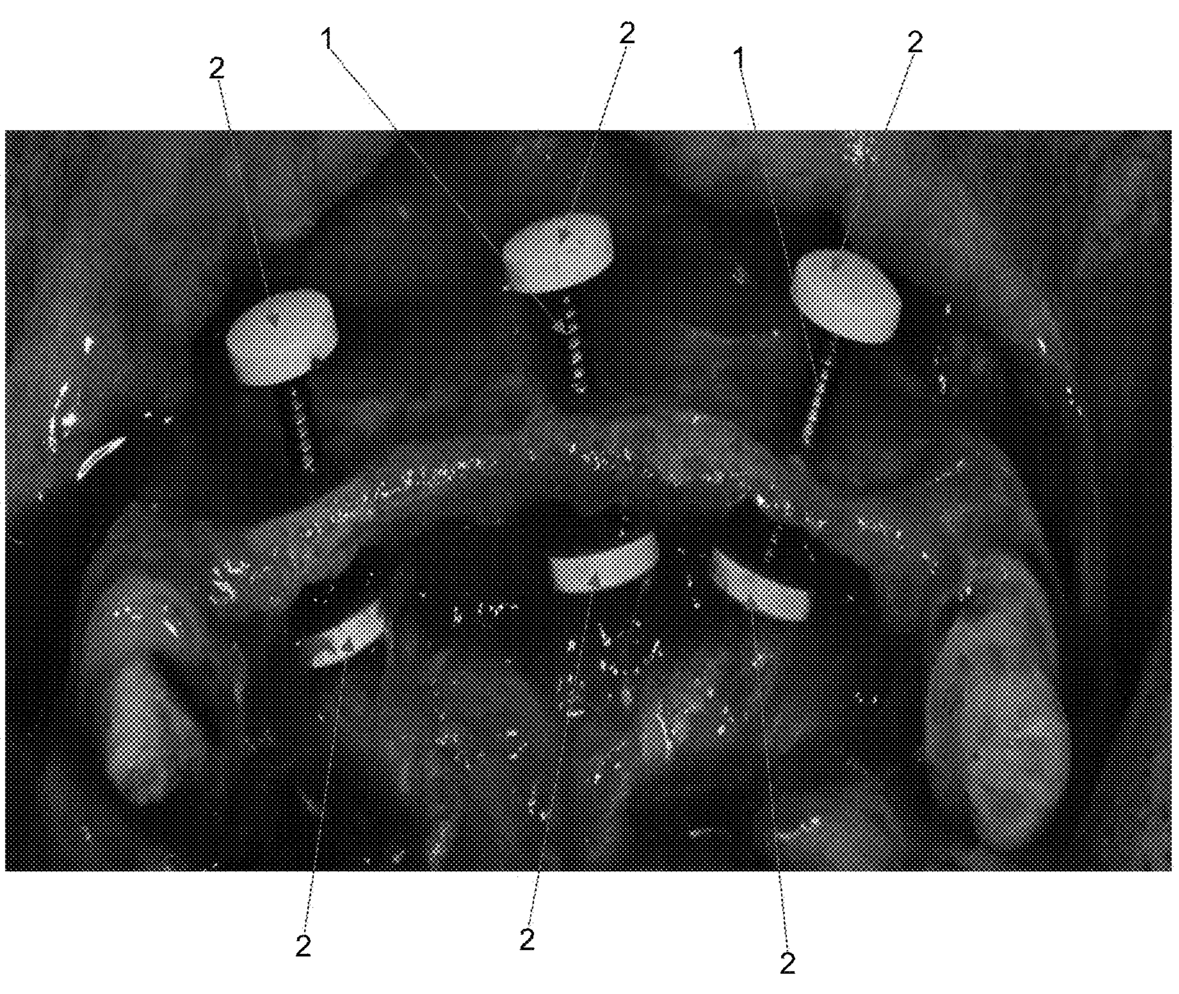
FIG. 6 shows the titanium screws fastened, with PEEK capsules adapted at both ends of the aforementioned screws.
Figure 7:
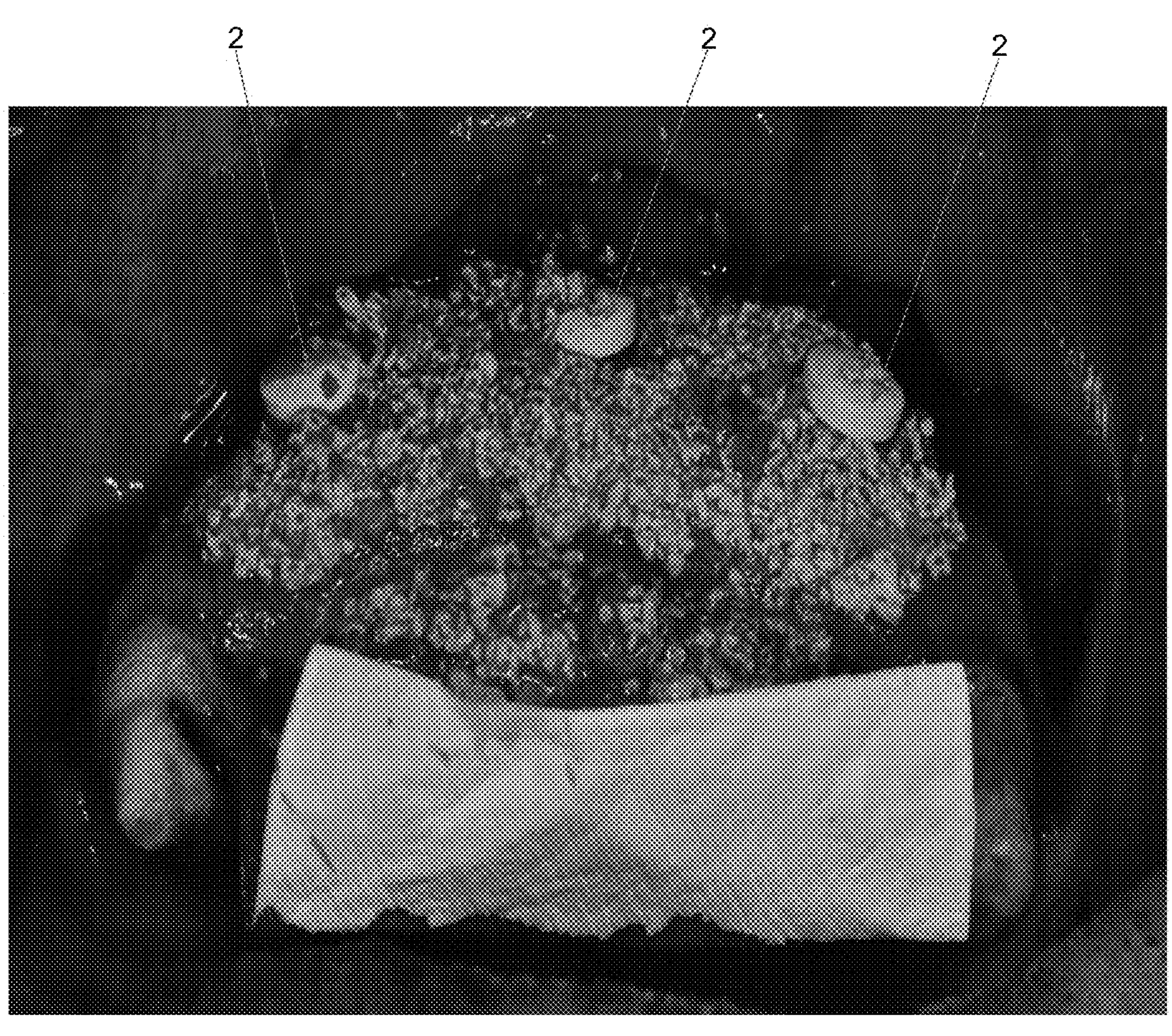
FIG. 7 shows, after installing the device, the insertion of the particulate bone graft.

Subsequently to creating minor perforations in the receiver bone to stimulate bleeding, three perforations were made with drills with 1.1 mm in diameter for inserting three titanium screws (1) of the device (FIG. 5). To insert these screws (1), specific drivers were used (which fit onto the head of the screws). In this clinical case, since the requirement was bidirectional augmentation, 10 mm screws (1) were used, transfastening the receiver bone, keeping about 5 mm of screw exposed by buccal and about 3 mm by palatal (since the thickness of the residual bone was about 2 mm). As soon as the screws (1) are fastened, PEEK capsules (2) are adapted at both ends of the screws, as shown in FIG. 6.

Figure 8:
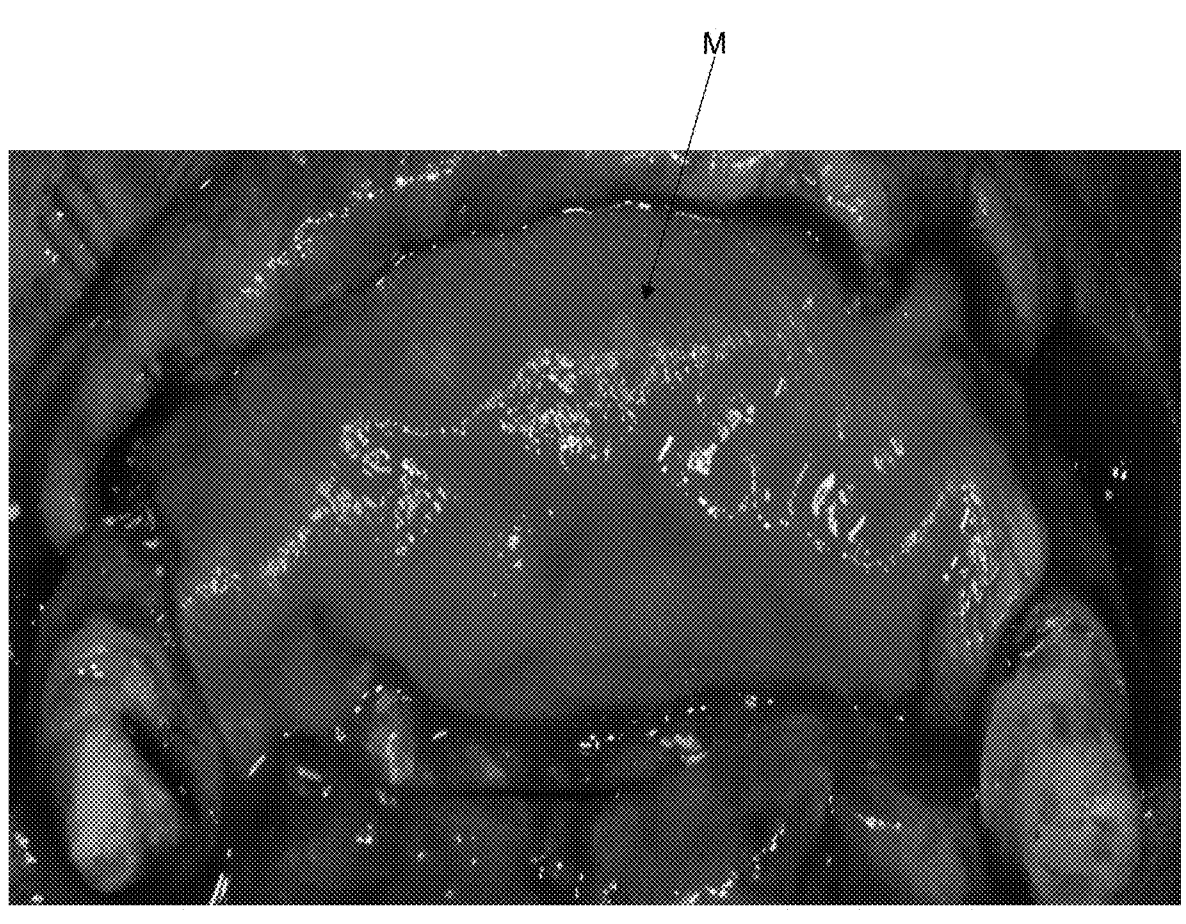
FIG. 8 shows the coating of the area of the preceding figure with resorbable hydrophilic membrane.

With the installation of the devices, the particulate bone graft (FIG. 7) is inserted and the area coated with resorbable hydrophilic membrane (M) (FIG. 8).

Figure 9:
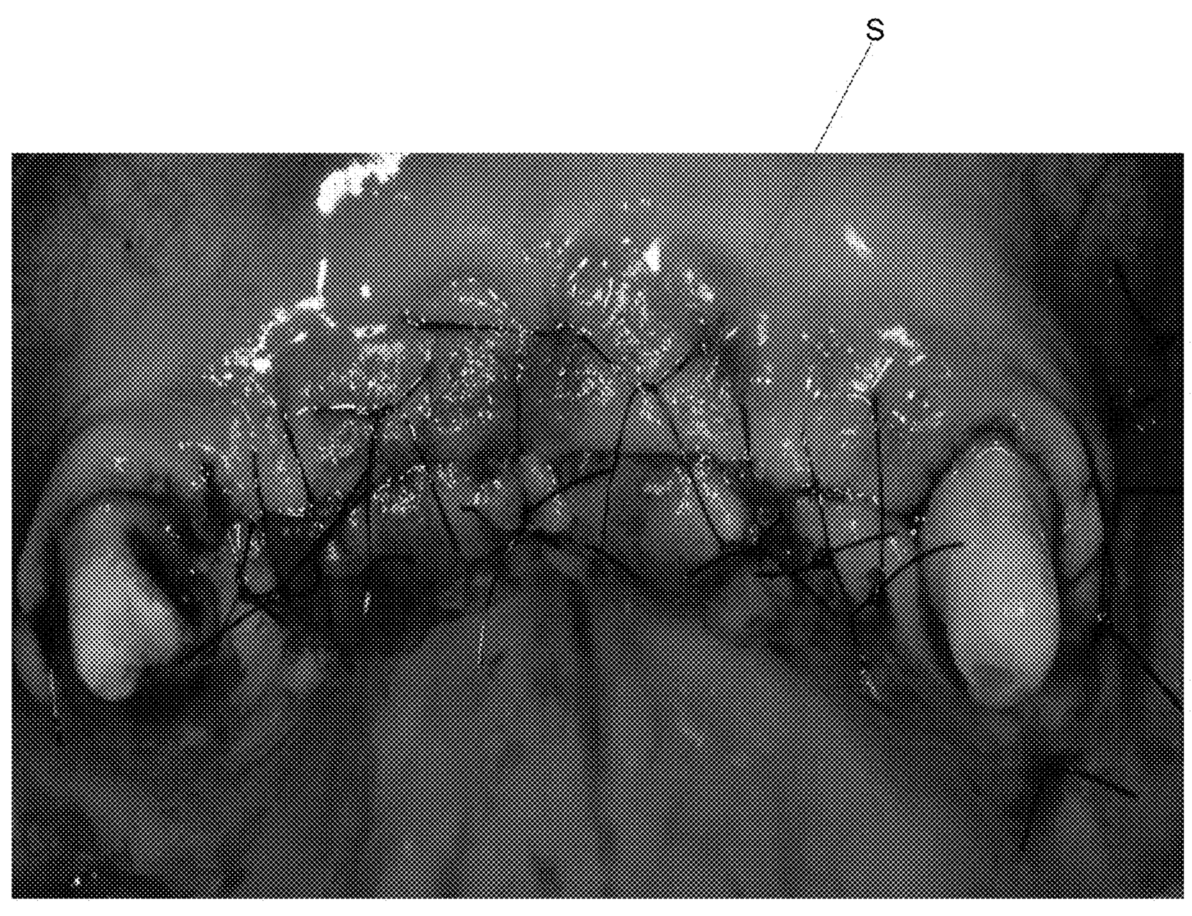
FIG. 9 shows the application of the suture.

FIG. 9 shows the suture(S) performed after conclusion of the stages described above.

Figure 10:
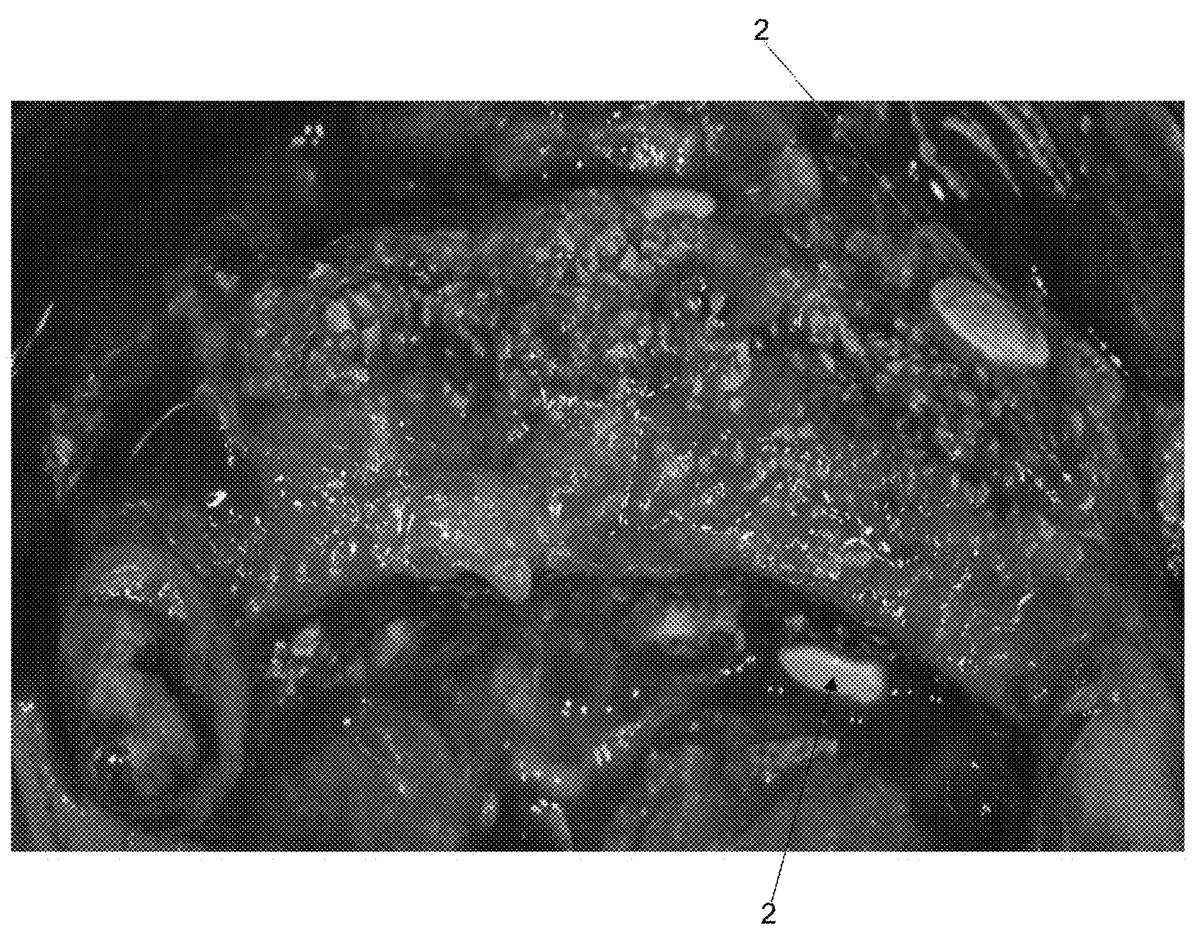
FIG. 10 shows the open region, after the bone healing period (about six months), for the removal of the devices of the invention.
Figure 11:
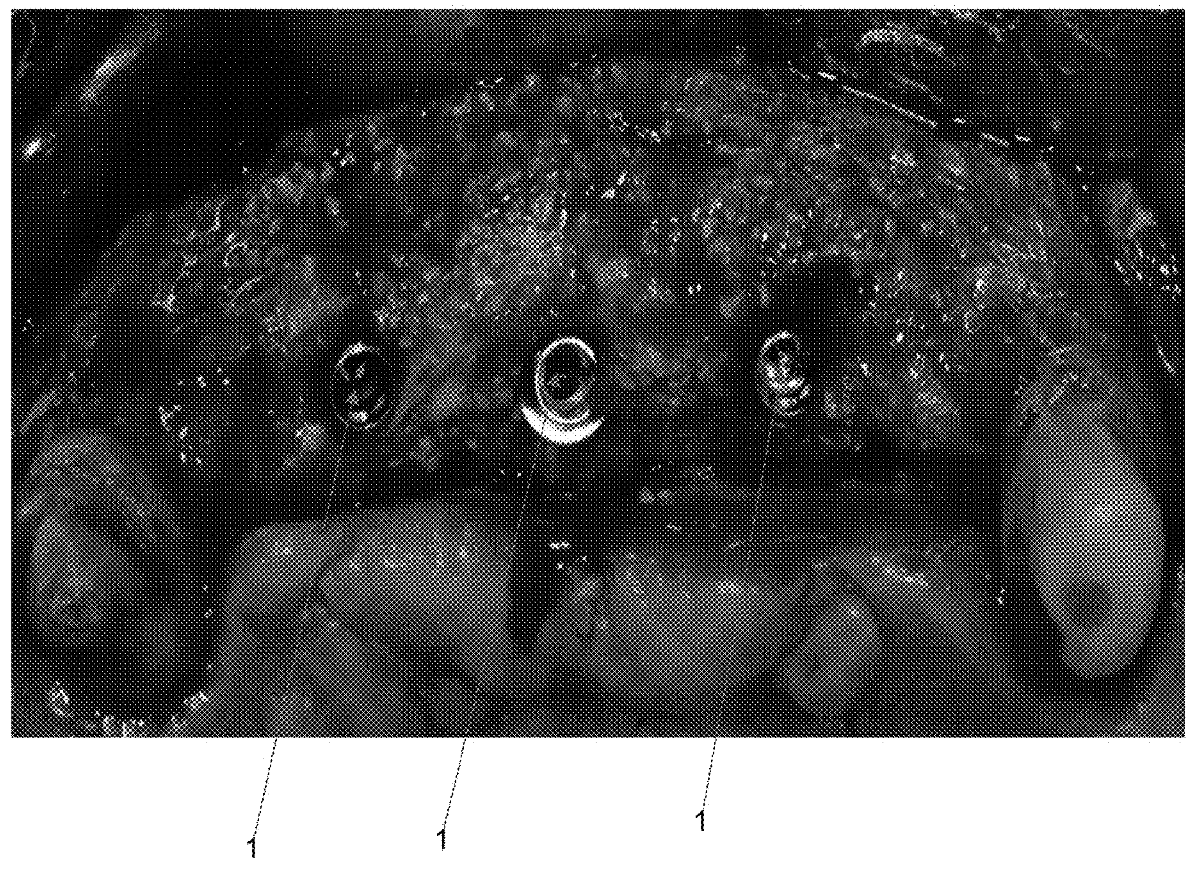
FIG. 11 shows the installation of the implants.

After the bone healing period (in this case about 6 months) the region is reopened to enable the removal of the devices and installation of the implants (FIGS. 10 and 11).

FIG. 12 shows a trans-operatory clinical image of the second clinical case, with significant unidirectional horizontal bone loss (just by buccal) and need for tissue reconstruction prior to installing the implants. This image shows the device already installed. A screw (1) just 6 mm in length was used since the need was for reconstruction of just one side (buccal). FIG. 13 shows the adaptation of the particulate bone graft.

FIG. 14 shows the coating with resorbable hydrophilic membrane (M). In this case, a PEEK capsule (2) was optionally adapted on the outside of the membrane, helping to immobilize it.

Figure 15:
FIG. 15 shows a pre-operatory clinical situation of a third clinical case, with significant unidirectional vertical and horizontal bone loss (buccal) and need for tissue reconstruction prior to installing the implants.

FIG. 15 illustrates a pre-operatory clinical situation of the third clinical case, with significant unidirectional vertical and horizontal bone loss (buccal) and need for tissue reconstruction prior to installing the implants.

Figure 16:
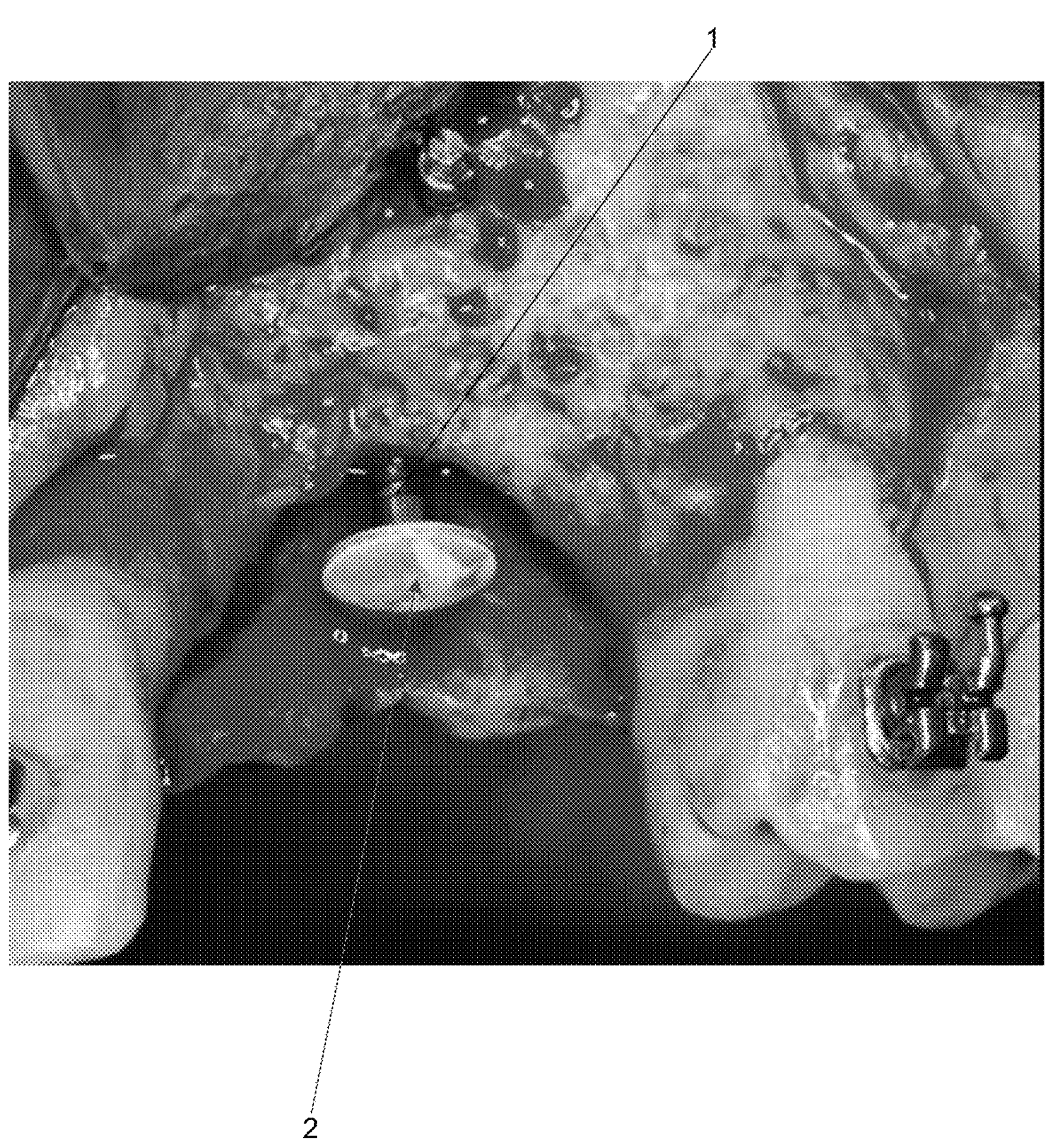
FIG. 16 shows, after surgical access, in the third clinical case, the installation of two devices (one to enable the vertical tissue decompression and the other horizontal), both screws 6 mm in length.
Figure 17:
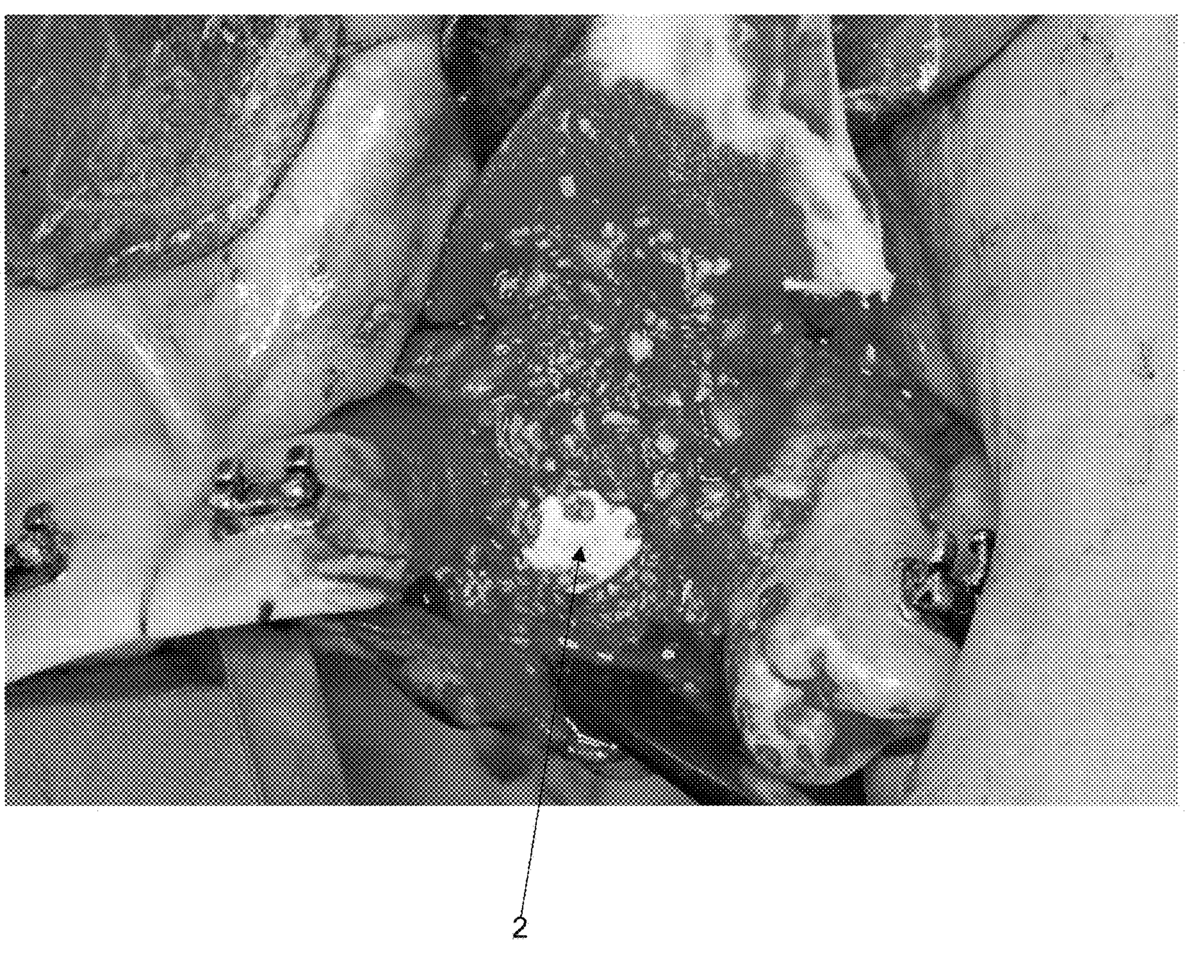
FIG. 17 shows, in the third clinical case, the bone graft positioned.

After surgical access, two devices were installed (one for enabling vertical tissue decompression and the other horizontal), as illustrated in FIG. 16. Both screws (1) were 6 mm in length.

Figure 18:
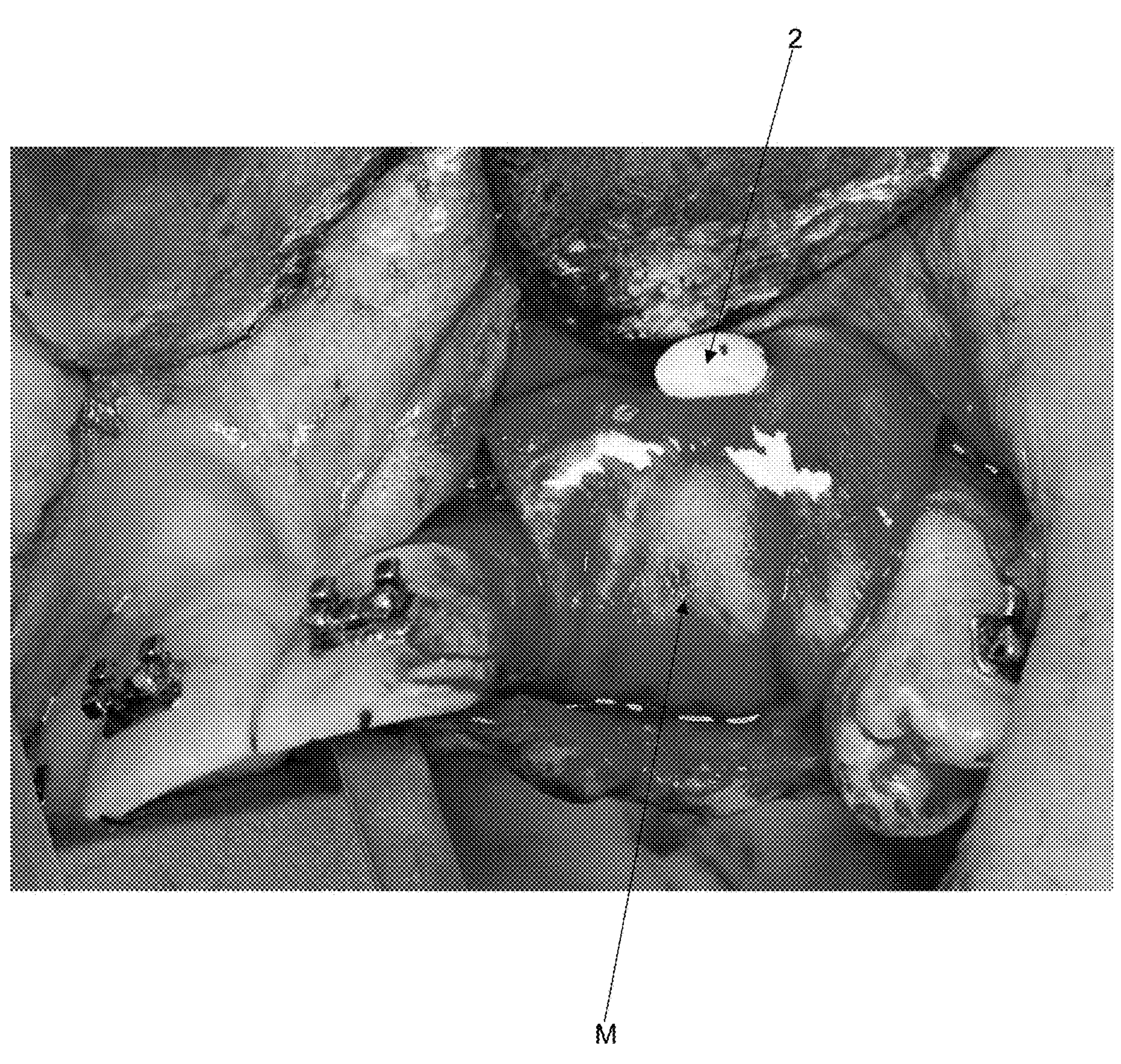
FIG. 18 shows, in the third clinical case, the arrangement of a resorbable hydrophilic membrane used to coat the entire grafted area.

Subsequently, the particulate bone graft was positioned (FIG. 17) and a resorbable hydrophilic membrane (M) was used to coat the entire grafted area (FIG. 18).

Figure 19:
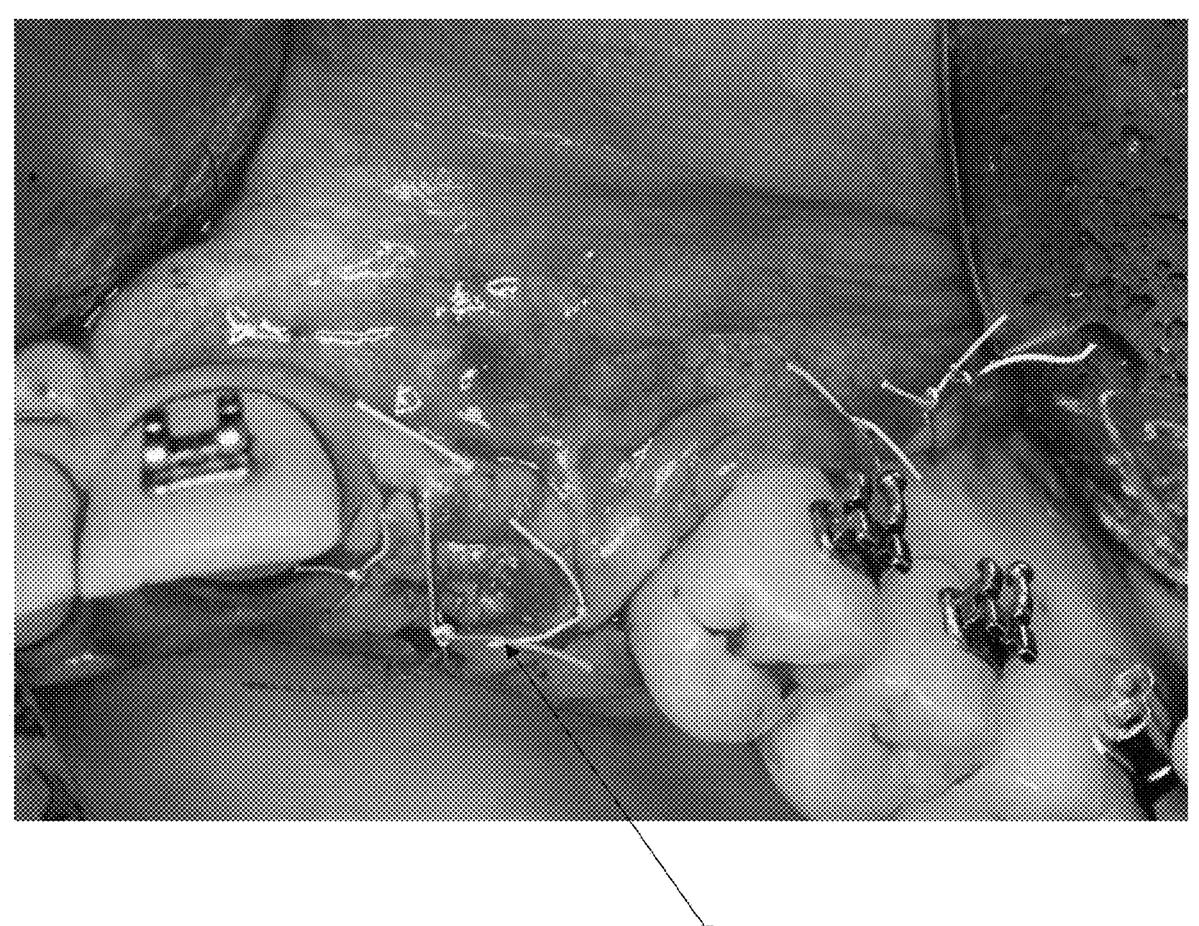
FIG. 19 shows, in the third clinical case, the sutured region.

FIG. 19 shows the region finally sutured(S), after the sequence of procedures described as of FIG. 15.

The three clinical cases presented illustrate the versatility of the art, based on using the device according to the invention, for usage in appositional bone augmentations both bidirectional horizontal (clinical case 1), and unidirectional horizontal (clinical case 2) and vertical (clinical case 3).

The invention claimed is:

1. A device for retracting soft tissue for appositional bone reconstruction surgeries in implantology, comprising:

a titanium screw having a pair of opposing hexagonal end fittings and an externally-threaded shaft extending therebetween; and a pair of caps, each cap configured to be removably coupled to one of the hexagonal end fittings of said titanium screw;

wherein each hexagonal end fitting includes a hexagonal prism portion at a distal end of the hexagonal end fitting, and a hexagonal frustum portion at a proximal end of the hexagonal end fitting, the hexagonal frustum portion flaring outward in a proximal direction;

wherein each cap is formed from PEEK and includes a domed distal face and a flat proximal face opposite the domed distal face; and wherein the titanium screw is configured to be transfastened through bone such that both hexagonal end fittings are exposed on opposite sides of the bone for subsequently receiving the pair of PEEK caps thereon so as to enable bidirectional horizontal bone augmentation.

2. The device for retracting soft tissue according to claim 1, wherein the flat proximal face of each cap comprises a central recess for receiving one of the hexagonal end fittings therein and configured to engage with the hexagonal end fitting.

3. The device for retracting soft tissue according to claim 2, wherein a diameter of the cap is 4.5 mm and a height of the cap is 1.5 mm.

4. The device for retracting soft tissue according to claim 2, wherein:

a diameter of the cap is 4.5 mm and a height of the cap is 1.5 mm; and dimensions of the titanium screw are selected from the group consisting of:

a length of the titanium screw is 10 mm and a length of the threaded shaft is 8 mm;

a length of the titanium screw is 8 mm and a length of the threaded shaft is 6 mm; and a length of the titanium screw is 6 mm and a length of the threaded shaft is 4 mm.

5. The device for retracting soft tissue according to claim 1, wherein a length of the titanium screw is 10 mm and a length of the threaded shaft is 8 mm.

6. The device for retracting soft tissue according to claim 1, wherein a length of the titanium screw is 8 mm and a length of the threaded shaft is 6 mm.

7. The device for retracting soft tissue according to claim 1, wherein a length of the titanium screw is 6 mm and a length of the threaded shaft is 4 mm.

8. A device for retracting soft tissue for appositional bone reconstruction surgeries in implantology, comprising:

a titanium screw having a pair of opposing hexagonal end fittings and an externally-threaded shaft extending therebetween; and a pair of caps, each cap configured to be removably coupled to one of the hexagonal end fittings of said titanium screw;

wherein each hexagonal end fitting includes a hexagonal prism portion at a distal end of the hexagonal end fitting, and a hexagonal frustum portion at a proximal end of the hexagonal end fitting, the hexagonal frustum portion flaring outward in a proximal direction;

wherein each cap is formed from PEEK and includes a domed distal face and a flat proximal face opposite the domed distal face, the flat proximal face further including a central recess for receiving the hexagonal end fitting therein and configured to engage with the hexagonal end fitting;

wherein the titanium screw is configured to be transfastened through bone such that both hexagonal end fittings are exposed on opposite sides of the bone for subsequently receiving the pair of PEEK caps thereon so as to enable bidirectional horizontal bone augmentation;

wherein a diameter of the cap is 4.5 mm and a height of the cap is 1.5 mm; and wherein dimensions of the titanium screw are selected from the group consisting of:

a length of the titanium screw is 10 mm and a length of the threaded shaft is 8 mm;

a length of the titanium screw is 8 mm and a length of the threaded shaft is 6 mm; and a length of the titanium screw is 6 mm and a length of the threaded shaft is 4 mm.

* * * * *